United States Patent
Chou

(10) Patent No.: US 8,268,242 B2
(45) Date of Patent: Sep. 18, 2012

(54) HYDROGEN SENSOR

(75) Inventor: Tai-Hsu Chou, Taipei Hsien (TW)

(73) Assignee: Hon Hai Precision Industry Co., Ltd., Tu-Cheng, New Taipei (TW)

( * ) Notice: Subject to any disclaimer, the term of this patent is extended or adjusted under 35 U.S.C. 154(b) by 837 days.

(21) Appl. No.: 12/346,813

(22) Filed: Dec. 30, 2008

(65) Prior Publication Data

US 2011/0184657 A1   Jul. 28, 2011

(30) Foreign Application Priority Data

May 22, 2008   (CN) .......................... 2008 1 0301725

(51) Int. Cl.
*G01N 33/00* (2006.01)
(52) U.S. Cl. ................. 422/68.1; 422/82.01; 422/82.02; 422/90
(58) Field of Classification Search ................. 422/68.1, 422/82.01, 82.02, 90
See application file for complete search history.

(56) References Cited

U.S. PATENT DOCUMENTS 7,833,801 B2 * 11/2010 Stasiak et al. ................. 436/149

OTHER PUBLICATIONS

Guo Miao, Pan Min, Chen Jinxia, Mi Yuhong, Zhang Xiaobin, Chen Yuquan, Palladium Modified Multi-walled Carbon Nanotube for Benzene Detect at Room Temperature, Chinese Journal of Analytical Chemistry, Dec. 2006, pp. 1755 to 1758, vol. 34 No. 12, China.
Jing Kong, Michael G. Chapline, Hongjie Dai, Functionial Carbon Nanotubes for Molecular Hydrogen Sensor, Advanced Materials, Sep. 2001, pp. 1384 to 1386, vol. 12 No. 18, Germany.

* cited by examiner

*Primary Examiner* — Sam P Siefke
(74) *Attorney, Agent, or Firm* — Altis Law Group, Inc.

(57) ABSTRACT

A hydrogen sensor includes a substrate, a hydrogen absorbing member, a power source, an ammeter, and a processing unit. The hydrogen absorbing member is positioned on the substrate, and includes a carbon nanotube yarn and a hydrogen absorbing film coated on the carbon nanotube yarn. The ammeter measures an electric current. The hydrogen absorbing member and the ammeter are connected in series to the power source. The processing unit is electrically coupled to the ammeter to obtain a hydrogen concentration according to the electric current.

4 Claims, 2 Drawing Sheets

HYDROGEN SENSOR

BACKGROUND

1. Technical Field

The disclosure relates to a hydrogen sensor.

2. Description of Related Art

Nowadays, a large amount of hydrogen is used in industrial and medical applications. Hydrogen is a flammable gas. If the hydrogen leaks, an explosion could occur. Therefore, typical hydrogen sensors are widely used in factories, laboratories and hospitals to accurately monitor the concentration of leaking hydrogen. However, the typical hydrogen sensors have low sensitivities and can not meet the demands.

Therefore, a new hydrogen sensor is desired to overcome the above-described shortcoming.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION OF THE EMBODIMENTS

Figure 1:
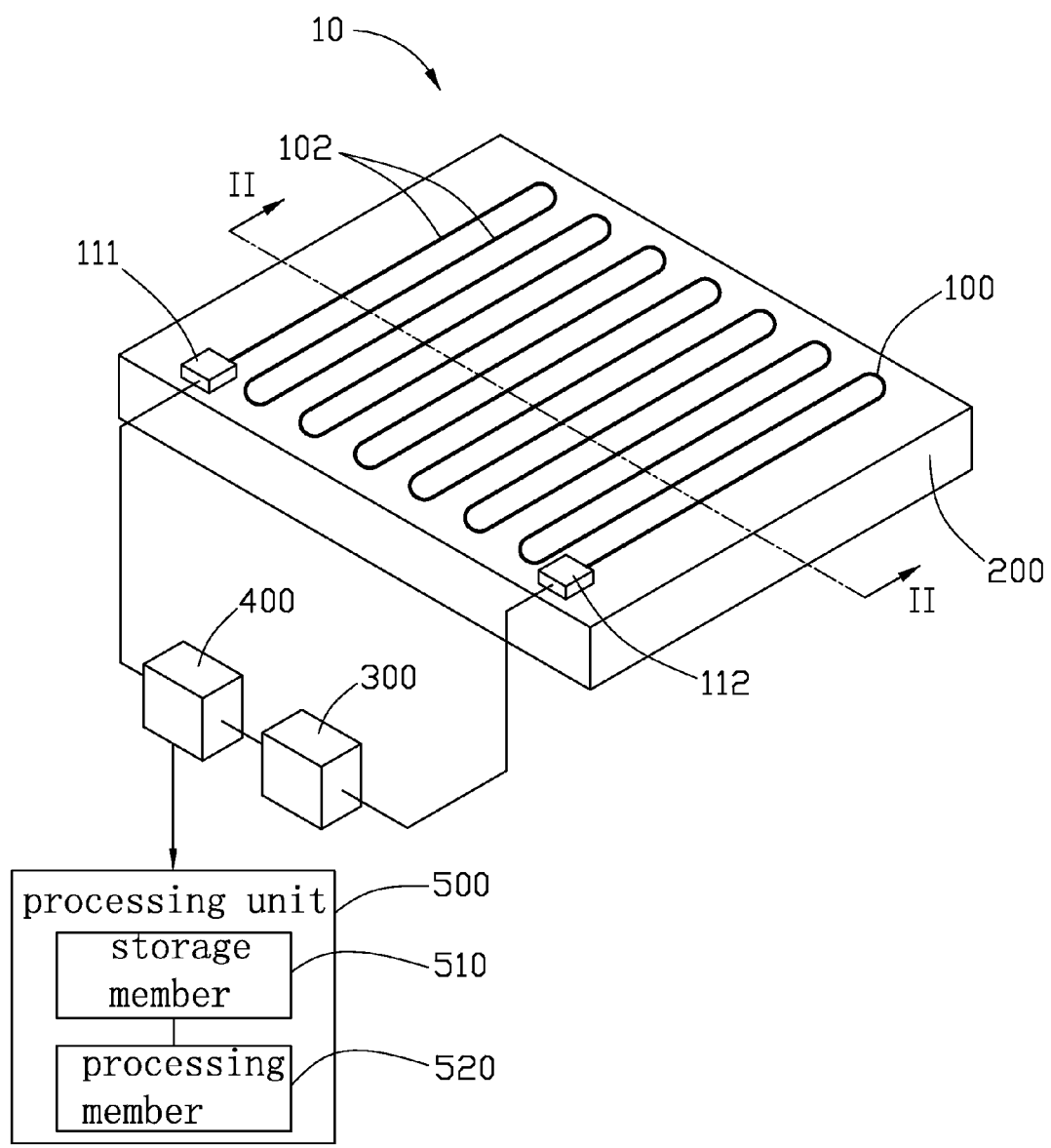
FIG. 1 is a perspective view of one embodiment of a hydrogen sensor.
Figure 2:
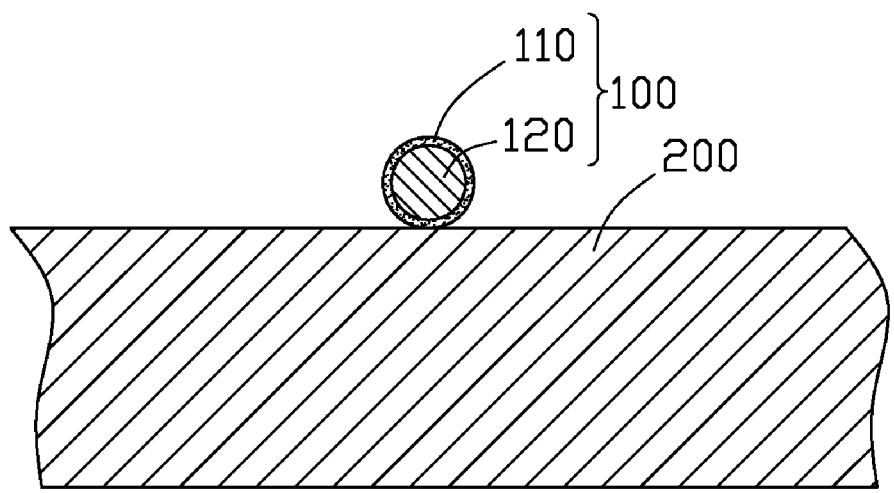
FIG. 2 is a partial, cross-sectional view of the hydrogen sensor of FIG. 1, taken alone line II-II.

Referring to FIGS. 1 and 2, one embodiment of a hydrogen sensor 10 includes a hydrogen absorbing member 100, a substrate 200, a power source 300, an ammeter 400, and a processing unit 500.

The hydrogen absorbing member 100 is positioned on the substrate 200. The ammeter 400 and the hydrogen absorbing member 100 are connected in series to the power source 300. The processing unit 500 is electrically coupled to the ammeter 400. In one embodiment, a first electrode 111 is positioned at one end of the hydrogen absorbing member 100 and electrically coupled to the ammeter 400. A second electrode 112 is positioned at another end of the hydrogen absorbing member 100 and electrically coupled to the power source 300.

The hydrogen absorbing member 100 is arranged to form a plurality of substantially parallel portions 102. The parallel portions 102 are substantially identical to each other. The hydrogen absorbing member 100 includes a carbon nanotube yarn 120 and a hydrogen absorbing film 110.

The carbon nanotube yarn 120 includes a plurality of carbon nanotube bundles joined end to end by van der Waals attractive forces. Each of the carbon nanotube bundles includes a plurality of carbon nanotubes substantially parallel to each other. The hydrogen absorbing film 110 is coated on the carbon nanotube yarn 120. In one embodiment, the hydrogen absorbing film 110 may contain palladium or palladium alloy.

The substrate 200 may be a silicon substrate. The power source 300 may be a constant current source. The ammeter 400 is configured to measure an electric current.

The processing unit 500 is configured to obtain a hydrogen concentration according to the electric current. The processing unit 500 includes a storage member 510 to store the data of a relationship between the electric current and the hydrogen concentration, and a processing member 520 to obtain an electric current from the ammeter 400 and read the data of the relationship between the electric current and the hydrogen concentration from the storage member 510 to calculate a hydrogen concentration. The data of the relationship between the electric current and the hydrogen concentration is pre-stored in the storage member 510.

In use, the carbon nanotube yarn 120 and the hydrogen absorbing film 110 is powered by the power source 300. The hydrogen absorbing film 110 absorbs hydrogen gas, whereby the resistance of the hydrogen absorbing film 110 varies. As a result, the electric current varies due to the varying resistance of the hydrogen absorbing film 110. The process member 520 obtains the electric current from the ammeter 400 and read the data of the relation between the electric current and the hydrogen concentration from the storage member 510 to calculate a hydrogen concentration.

The carbon nanotube yarn 120 has high electric conductivity and a large specific surface area, such that the hydrogen sensor 10 has high sensitivity.

It is believed that the present embodiments and their advantages will be understood from the foregoing description, and it will be apparent that various changes may be made thereto without departing from the spirit and scope of the embodiments or sacrificing all of its material advantages.

What is claimed is:

1. A hydrogen sensor, comprising:
   a substrate;
   a hydrogen absorbing member positioned on a surface of the substrate, and comprising a carbon nanotube yarn and a hydrogen absorbing film coated on the carbon nanotube yarn, a lengthwise direction of the carbon nanotube yarn being substantially parallel to the surface of the substrate;
   a power source;
   an ammeter to measure an electric current, wherein the hydrogen absorbing member and the ammeter are connected in series to the power source; and
   a processing unit electrically coupled to the ammeter to obtain a hydrogen concentration according to the electric current;
   wherein the carbon nanotube yarn comprises a plurality of carbon nanotube bundles joined end to end by van der Waals attractive forces.

2. The hydrogen sensor of claim 1, wherein each of the carbon nanotube bundles comprises a plurality of carbon nanotubes substantially parallel to each other.

3. A hydrogen sensor, comprising:
   a substrate;
   a hydrogen absorbing member positioned on a surface of the substrate, arranged to form a plurality of substantially parallel portions, and comprising a carbon nanotube yarn and a hydrogen absorbing film coated on the carbon nanotube yarn and containing palladium or palladium alloy, a lengthwise direction of the carbon nanotube yarn being substantially parallel to the surface of the substrate;
   a power source;
   an ammeter to measure an electric current, wherein the hydrogen absorbing member and the ammeter are connected in series to the power source; and
   a processing unit electrically coupled to the ammeter to obtain a hydrogen concentration according to the electric current;
   wherein the carbon nanotube yarn comprises a plurality of carbon nanotube bundles joined end to end by van der Waals attractive forces.

4. The hydrogen sensor of claim 3, wherein each of the carbon nanotube bundles comprises a plurality of carbon nanotubes substantially parallel to each other.

* * * * *